United States Patent [19]

Burdeska et al.

[11] Patent Number: 5,084,570

[45] Date of Patent: Jan. 28, 1992

[54] PROCESS FOR THE PREPARATION OF 2-(2',4'-DIHYDROXYPHENYL)-4,6-DIARYL-S-TRIAZINES

[75] Inventors: Kurt Burdeska, Basle; Franz Günter, Riehen, both of Switzerland

[73] Assignee: Ciba-Geigy Corporation, Ardsley, N.Y.

[21] Appl. No.: 510,494

[22] Filed: Apr. 18, 1990

[30] Foreign Application Priority Data

Apr. 21, 1989 [CH] Switzerland .......................... 1536/89

[51] Int. Cl.$^5$ .......................................... C07D 251/24
[52] U.S. Cl. ................................... 544/216; 544/217; 544/219
[58] Field of Search .................. 544/216, 217, 219

[56] References Cited

U.S. PATENT DOCUMENTS

| | | | |
|---|---|---|---|
| 3,118,887 | 1/1964 | Hardy | 544/216 |
| 3,242,175 | 3/1966 | Duennenberger | 544/216 |
| 3,268,474 | 8/1966 | Hardy | 544/216 |

OTHER PUBLICATIONS

Ciba I, "1,3,5-triazine aryl derivatives" CA 62:4041h (1965).
Ciba II, "4-(2-hydroxy-4-alkoxyphenyl) etc." CA 9155h (1965).
Duennenberger et al. "o-hydroxphenyl-s-triazine" CA 72:79103d (1970).
Helv. 55, 1566ff (1972).
Rec.Trav.Chim.Pays Bas 78,967ff (1959).

*Primary Examiner*—Patricia L. Morris
*Attorney, Agent, or Firm*—Kevin T. Mansfield; Edward McC.Roberts

[57] ABSTRACT

There is disclosed a process for the preparation of 2-(2',4'-dihydroxyphenyl)-4,6-diaryl-s-triazines of formula (1) as indicated in claim 1, which process comprises reacting, in a first step, a compound of formula (4) as indicated in claim 1, with the aid of a Lewis acid, in the presence of xylene or toluene, with a substituted benzene of formula (5) as indicated in claim 1, and, in a second step, reacting the resultant compound of formula (2) as indicated in claim 1, in the presence of toluene or xylene, with chlorine or sulfuryl chloride, to give the compound of formula (3) as indicated in claim 1, and, in a third step, reacting the resultant compound with 1,3-dihydroxybenzene, with the aid of a Lewis acid, to give the compound of formula (1), in the presence of toluene, xylene or a mixture of xylene isomers.

6 Claims, No Drawings

PROCESS FOR THE PREPARATION OF 2-(2',4'-DIHYDROXYPHENYL)-4,6-DIARYL-S-TRIAZINES

The present invention relates to a novel process for the preparation of 2-(2',4'-dihydroxyphenyl)-4,6-diaryl-s-triazines.

Asymmetrically substituted dihydroxyphenyl-s-triazines are disclosed, for example, in U.S. Pat. No. 3,268,474. These compounds are obtained by reacting firstly 1 mol of cyanuric chloride, in the presence of a Friedel-Crafts catalyst, with 2 mol of dimethyl benzene, and then reacting the resultant monochloroaryltriazine in a further Friedel-Crafts reaction with dihydroxybenzene. The solvents used for this reaction are nitrobenzene, o-dichlorobenzene (oDCB), chlorobenzene or highly chlorinated solvents. The selectivity of the Friedel-Crafts reaction of s-trichlorotriazine with aromatic hydrocarbons, however, is poor. In addition to the monochlorodiaryltriazines, mixtures of dichloroaryltriazines and triaryltriazines which are very difficult to separate are formed [Helv. 55, 1589 (1972)].

A process has now been found by means of which it is possible to prepare 2-(2',4'-dihydroxyphenyl)-4,6-diaryl-s-triazines in simple manner and in very good yield.

The process of this invention for the preparation of 2-(2',4'-dihydroxyphenyl)-4,6-diaryl-s-triazines of formula

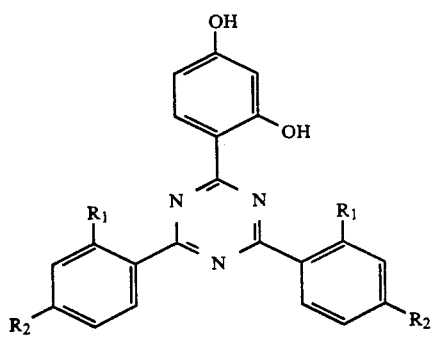

wherein $R_1$ is $C_1$–$C_4$alkyl or hydrogen and $R_2$ is $C_1$–$C_4$alkyl, by replacing the methylthio group of a methylthio-s-triazine of formula

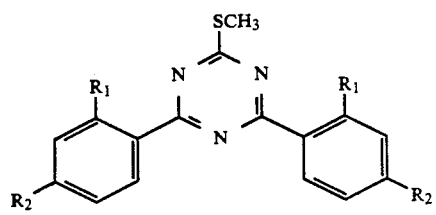

wherein $R_1$ and $R_2$ are as defined for formula (1), by a chlorine atom, and by reacting the resultant compound of formula

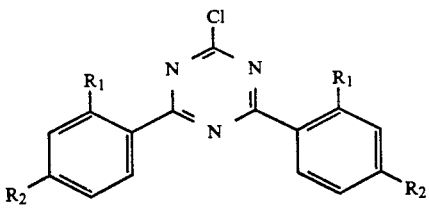

wherein $R_1$ and $R_2$ are as defined for formula (1), with 1,3-dihydroxybenzene, with the aid of a Lewis acid, to give a compound of formula (1), comprises reacting, in a first step, the compound of formula

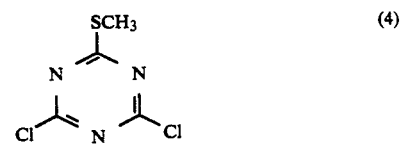

with the aid of a Lewis acid, in the presence of xylene or toluene, with a substituted benzene of formula

wherein $R_1$ and $R_2$ are as defined for formula (1), and, in a second step, reacting the resultant compound of formula (2), in the presence of xylene or toluene, with chlorine or sulfuryl chloride, to give the compound of formula (3), and, in a third step, reacting the resultant compound with 1,3-dihydroxybenzene, with the aid of a Lewis acid, to give the compound of formula (1), in the presence of toluene, xylene or a mixture of xylene isomers.

In this specification, the term "aryl" will be understood as meaning tolyl or xylyl.

It is preferred to use aluminium chloride as Lewis acid for the preparation of the compounds of formula (1) and (2).

$C_1$–$C_4$Alkyl radicals $R_1$ and $R_2$ are, typically, methyl, ethyl, n-propyl, butyl, isobutyl, sec-butyl or tert-butyl, or preferably $R_1$ is hydrogen or methyl and $R_2$ is methyl.

Particularly interesting compounds are those in which $R_1$ is hydrogen and $R_2$ is methyl, or those in which $R_1$ and $R_2$ are methyl.

The diaryl monochlorotriazine of formula (3) can also be obtained from compound (4) without isolation of the methylthio intermediate of formula (2) in a one pot process.

The reaction temperatures of the individual steps may vary within wide ranges, for example from 30° to 100° C. The first step of the reaction is carried out in the temperature range from 55° to 90° C., the second step in the range from 0° to 80° C., and the third step in the range from 60° to 100° C.

Preferred reaction temperatures are, for the first step, in the range from 65° to 75° C., for the second step from 40° to 50° C. and, for the third step, from 80° to 90° C.

The preparation of the starting compound of formula (4) is effected by reacting cyanuric chloride with methyl mercaptan. This reaction is described in detail in Rec. Trav. chim. Pays Bas 78, 967 (1959).

The use of dichloromethylthio-s-triazine in place of the corresponding methoxy compound has the advantage that, in the Friedel-Crafts reaction with the substituted benzene of formula (5), the diaryl-s-triazine of formula (2) is formed selectively. In the corresponding Friedel-Crafts reaction of dichloromethoxy-s-triazine, however, a dealkylation of the methoxy group always takes place [Helv. 55, 1575 (1972)].

The methylthio-s-triazines of formula (2) prepared in the first step of the process of this invention are novel compounds, provided $R_1$ is not hydrogen if $R_2$ is methyl.

The reaction of the second step, in which the methylthio group of the compounds of formula (2) is replaced by a chlorine atom, is described in Chem. Ber. 100, 1874 (1967). Whereas in this publication the reaction is carried out in carbon tetrachloride, the process of this invention takes place in toluene or xylene.

The compounds of formula (3) formed in the second step of the reaction are also known from Helv. 55, 1589 (1972).

The Friedel-Crafts reaction of monochlorodiphenyl triazines with dihydroxybenzene, which corresponds to the reaction of the third step, is described in numerous references, for example in U.S. Pat. No. 3,268,474; but the reaction is carried out in all references in nitrobenzene, oDCB or chlorobenzene. However, in the process of the present invention, this reaction is always carried out in toluene, xylene or mixtures of xylene isomers, without any reaction with the solvent ensuing. This is a very surprising feature.

The process of this invention describes a novel route for the synthesis of asymmetrical dihydroxyphenyl-s-triazines, wherein all reaction steps are carried out in a single solvent and the products are obtained in high yield.

The compounds prepared by the process of this invention find utility as UV absorbers or they are starting materials for the synthesis of UV absorbers.

The following Examples will serve to illustrate the invention.

EXAMPLE 1

293 g of anhydrous aluminium chloride (sublimed, ex Merck) are suspended in 600 ml of toluene and the suspension is heated to 70°-75° C. With stirring, a solution of 200.1 g of 2,4-dichloro-6-methylthio-1,3,5-triazine in 550 ml of toluene is run into the above suspension over 1.5 hours. During this addition, the temperature should not exceed 80° C. The reaction mixture is then heated to 85°-90° C. and stirring is continued for 5.5 hours at this temperature. The mixture is allowed to cool to 50° C. and then stirred into 600 ml of water and 150 ml of 30% hydrochloric acid with cooling, such that the temperature remains in the range from 50°-60° C. The batch is then refluxed and the toluene is removed by steam distillation. The product is isolated while still warm, washed with hot water and then with methanol and dried, giving 280 g (91.2% of theory) of the compound of formula

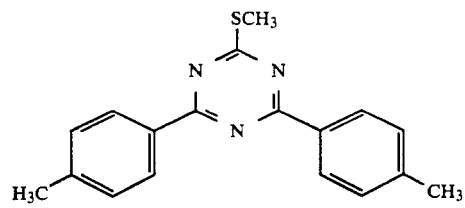

with a melting point of 161°-163° C. Carrying out the same procedure, but using 600 ml of xylene in place of 600 ml of toluene, gives the compound of formula

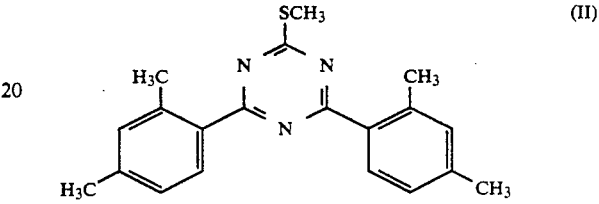

with a melting point of 82°-83° C.

EXAMPLE 2

280 g of anhydrous aluminium chloride (sublimed, ex Merck) are suspended in 600 ml of m-xylene and the suspension is heated to 65°-70° C. With good stirring, a solution of 200.1 g of 2,4-dichloro-6-methylthio-1,3,5-triazine (98%) in 420 ml of m-xylene is run into the above suspension over 1.5 hours at 65°-70° C. The reaction mixture is then stirred at 65°-70° C. for 1.5 hours to bring the reaction to completion. The reaction mixture is allowed to cool to 50° C. and then stirred into 900 ml of water and 100 ml of 30% hydrochloric acid. During this addition, the temperature should not exceed 80° C. After stirring for a further 10 minutes, the aqueous phase is separated from the xylene layer. After cooling to 35°-40° C., 140 g of chlorine are then introduced into the xylene layer containing 2-methylthio-4,6-bis(2',4'-dimethylphenyl)-1,3,5-triazine over 2 hours, whereupon 2-chloro-4,6-bis(2',4'-dimethylphenyl)-1,3,5-triazine precipitates. The precipitate is isolated by filtration at 0°-5° C., washed with xylene and petroleum ether and dried, giving 266 g (82.1% of theory) of the compound of formula

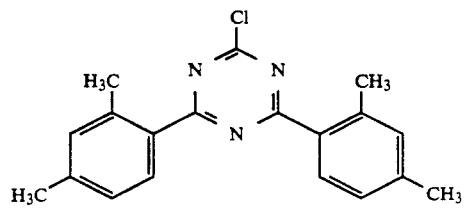

with a melting point of 134°-136° C.

The compound of formula

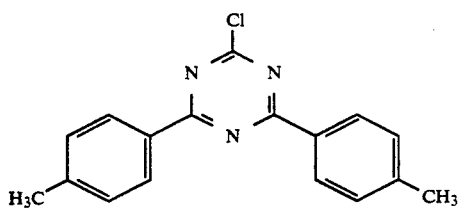

prepared in analogous manner using toluene in place of m-xylene has a melting point of 204°-206° C.

EXAMPLE 3

The compound of formula (IV) can also be prepared in the following manner: 30.7 g of 2-methylthio-4,6-bis(4'-methylphenyl)-1,3,5-triazine are suspended in 70 ml of toluene and the suspension is heated to 55°-60° C. With good stirring, a solution of 27 g of sulfuryl chloride in 20 ml of toluene is run in over 40 minutes. The reaction is then stirred for 30 minutes at 60° C., thereafter cooled to 5° C., and the precipitated product is isolated by filtration. The filter product is washed with toluene and dried at 80° C. under vacuum. Yield: 25.3 g. The product has a melting point of 204°-206° C.

EXAMPLE 4

161.9 g of 2-chloro-4,6-bis(2',4'-dimethylphenyl)-s-triazine and 73.4 g of anhydrous aluminium chloride are added in succession to 400 ml of a mixture of xylene isomers. The suspension is heated to 70°-75° C. and, at this temperature, a suspension of 66 g of resorcinol and 100 ml of a mixture of xylene isomers are run in over 1.5 hours. The suspension is heated for 1 hour to 85°-90° C. and stirred at this temperature for 3 hours. The reaction mixture is cooled to 60° C. and then run into 400 ml of water and 100 ml of 30% hydrochloric acid. The mixture of xylene isomers is removed by distillation and the yellow product is isolated hot by filtration, washed with hot water and methanol and dried, giving 175-177 g (88-89% of theory) of the compound of formula

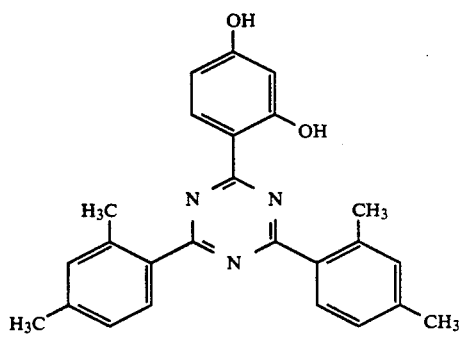

with melting point of 199°-201° C.

The compound of formula

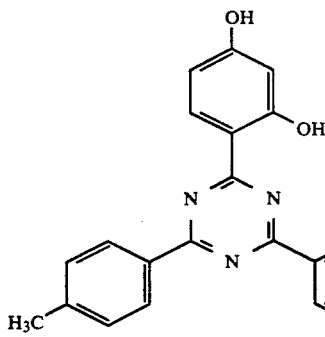

prepared in analogous manner using toluene in place of m-xylene has a melting point of 292°-293° C.

What is claimed is:

1. A process for the preparation of a 2-(2',4'-dihydroxyphenyl)-4,6-diaryl-s-triazine of formula

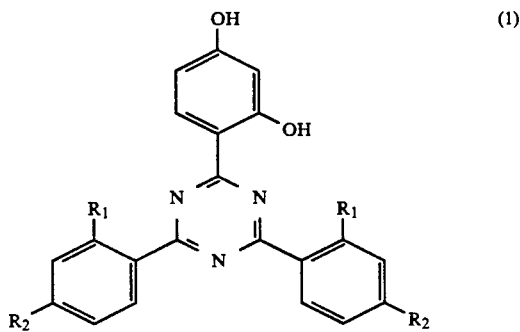

wherein $R_1$ is $C_1$-$C_4$alkyl or hydrogen and $R_2$ is $C_1$-$C_4$alkyl, by replacing the methylthio group of a methylthio-s-triazine of formula

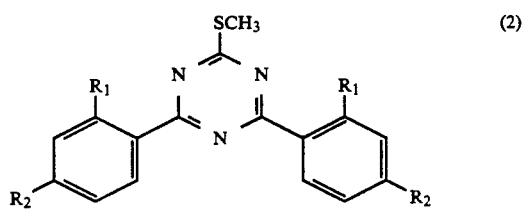

wherein $R_1$ and $R_2$ are as defined above, by a chlorine atom and by reacting the resultant compound of formula

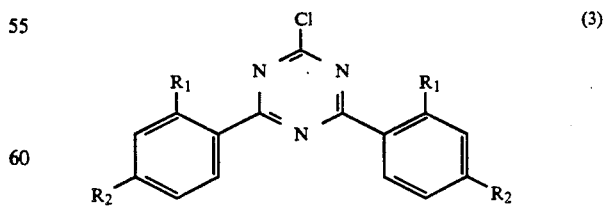

wherein $R_1$ and $R_2$ are as defined above, with 1,3-dihydroxybenzene, with the aid of aluminum chloride, to give a compound of formula (1), which process comprises reacting, in a first step, the compound of formula

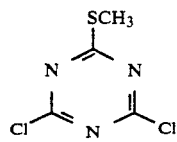

(4)

with the aid of aluminum chloride, in the presence of xylene or toluene, with a substituted benzene of formula

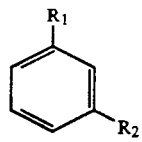

(5)

wherein $R_1$ and $R_2$ are as defined above, and, in a second step, reacting the resultant compound of formula (2), in the presence of xylene or toluene, with chlorine or sulfuryl chloride, to give the compound of formula (3), and, in a third step, reacting the resultant compound with 1,3-dihydroxybenzene, with the aid of aluminum chloride, to give the compound of formula (1), in the presence of toluene, xylene or a mixture of xylene isomers.

2. A process according to claim 1, wherein $R_1$ is hydrogen and $R_2$ is methyl.

3. A process according to claim 1, wherein $R_1$ and $R_2$ are methyl.

4. A process according to claim 1, wherein the compound of formula (3) is prepared without isolation of the compound of formula (2).

5. A process according to claim 1, wherein the reaction temperature of the first step of the reaction is in the range from 55° to 90° C., that of the second step is in the range from 0° to 80° C., and that of the third step is in the range from 60° to 100° C.

6. A process for the preparation of compounds of formula (1) by reacting a compound of formula (3) with 1,3-dihydroxybenzene, with the aid of aluminum chloride which process comprises carrying out the reaction in the presence of toluene, xylene or a mixture of xylene isomers.

* * * * *